United States Patent

Reyes et al.

[11] Patent Number: 6,107,023
[45] Date of Patent: Aug. 22, 2000

[54] DNA AMPLIFICATION AND SUBTRACTION TECHNIQUES

[75] Inventors: Gregory R. Reyes; Jungsuh Kim, both of Palo Alto, Calif.

[73] Assignee: Genelabs Technologies, Inc., Redwood City, Calif.

[21] Appl. No.: 07/208,512

[22] Filed: Jun. 17, 1988

[51] Int. Cl.[7] .............................. C12Q 1/68; C12P 19/34; C07H 21/02; C07H 21/04

[52] U.S. Cl. ............................ 435/6; 435/91.1; 435/91.2; 536/24.2; 536/24.3; 536/24.33; 536/25.4

[58] Field of Search .................... 435/6.91, 199, 435/252.3, 91.1, 91.2; 436/501; 536/27, 28, 24.2, 24.3, 24.33, 25.4; 935/4, 6, 16, 19, 77, 78

[56] References Cited

U.S. PATENT DOCUMENTS 4,683,195  7/1987  Mullis et al. .............................. 435/91

FOREIGN PATENT DOCUMENTS 0224126  6/1987  European Pat. Off. .................. 435/91

OTHER PUBLICATIONS

Maniatis et al., Molecular Cloning: A Laboratory Manual, Cold Spring Harbor, NY, 1982.

*Primary Examiner*—Stephanie W. Zitomer
*Attorney, Agent, or Firm*—Peter J. Dehlinger

[57] ABSTRACT

A method of isolating genomic or RNA-derived duplex fragments which are unique to one of two fragment mixtures. The fragments in positive-source and negative-source mixtures are separately equipped with end linkers, and each mixture is amplified by successive primed-strand replications, using a single primer which is homologous to the associated linker. The second-source linker is biotinylated, and the fragments in this mixture are hybridized in molar excess with the fragments in the positive-source mixture. DNA species which are not hybridized with the biotinylated species, i.e., species that are unique to the positive-source mixture, are isolated after removal of hybridized species by affinity chromatography. Also disclosed is a method of amplifying a mixture of DNA fragments by repeated linker/primer replication.

14 Claims, 4 Drawing Sheets

DNA AMPLIFICATION AND SUBTRACTION TECHNIQUES

1. FIELD OF THE INVENTION

The present invention relates to methods of isolating DNA fragments which are unique to one of two fragment mixtures, and in particular, to a method in which the fragments have been amplified by a novel linker/primer procedure.

2. REFERENCES

Anderson, M. L. M., and Young, B. D., in *Nucleic Acid Hybridization: A Practical Approach*, B. D. Hames and S. J. Higgins, eds., IRL Press, Oxford (1985), 73.

Britten, R. J. and Davidson, E. H., in *Nucleic Acid Hybridization: A Practical Approach*, B. D. Hames and S. J. Higgins, eds., IRL Press, Oxford (1985), 3.

Britten, R. J. and Kohne, D. E., *Science*, (1968), 161:529.

Davidson, E., in *Gene Activity in Early Development*, Academic Press, N.Y. (1976).

Hames, B. D. and Higgins, S. J., eds., *Nucleic Acid Hybridization: A Practical Approach*, IRL Press, Oxford (1985).

Kauffman, R. S. and Fields, B. N., in *Fundamental Virology*, B. N. Fields and D. M. Knipe, eds., Raven Press, New York (1986) 161.

Kohne, D. E., et al, *Biochemistry* (1977) 16(2):5329.

Maniatis, T., et al, *Molecular Cloning: A Laboratory Manual*, Cold Spring Harbor Laboratory (1982), 280.

Stanbury, J. B., et al, eds., *The Metabolic Basis of Inherited Disease*, McGraw-Hill Book Company, New York (1978).

Thompson, J., et al, *Anal Biochem* (1987) 303:334.

3. BACKGROUND OF THE INVENTION

The ability to identify and isolate nucleic acid sequences which are unique to one of two cellular or body-fluid sources has important applications in medicine. One application is in understanding and predicting certain disease states, based on the presence or absence of a given messenger RNA (mRNA) species. For example, an absent or altered mRNA coding for a specific protein in a particular cell type is often the direct cause of a hereditary disease, while the presence of an added mRNA species may signal the beginning of malignant transformation or the latent presence of an otherwise undetectable infectious agent. Although some hereditary diseases—such as sickle cell anemia, other hemoglobinopathies and the thalassemias—are due to changes in the nature or presence of high-abundance mRNAs, a large percentage of hereditary diseases have been shown to be or are likely to be caused by the absence of or alterations in specific proteins coded for by low-abundance mRNAs. These include Lesch-Nyhan Syndrome, Hunter's Syndrome, Hurler's Syndrome, Tay-Sachs Disease and adenosine deaminase deficiency, among others (Stanbury).

It is also known that several oncogenes exist whose aberrant activation leads to malignant transformation (Van Beverow), and the detection of changes in mRNA species will have important applications in the early detection of such transformation.

Another application of unique-sequence isolation methods is in the diagnosis and study of viral or other cell or fluid borne agents. For example, the transcription of virus-specific mRNA(s) may be the first indication of reactivation of a latent viral infection (Kauffman). The method may also be used to isolate and identify viral agents.

Methods of isolating unique genomic sequences have applications to the study of gene expression during cell activation, embryonic development or cell cycle progression, and for analyzing genetic diseases which are related to the presence or absence of disease-related genomic regions.

One major problem in the detection and isolation of unique mRNAs, complementary DNAs (cDNAs), or genomic fragments, is interference caused by numerous high-abundance species present in the source material. For example, in any given cell type, there may be 10,000–30,000 distinct mRNA species (Davidson), and these can range in concentration from several hundred thousand molecules per cell, for high-abundance species, to only a few molecules per cell, for low-abundance species. Thus, if the unique species of interest has a relatively low-abundance, the ratio of unique species may be as low as 1 in $10^6$.

A number of nucleic acid hybridization techniques aimed at isolating and analyzing unique nucleic acid species have been developed heretofore. These techniques rely on the ability of denatured nucleic acids to reassociate in a sequence specific manner by Watson-Crick base pairing interactions (Britten 1968, 1985). The rate at which renaturation occurs is determined by the sequence complexity of the sample, the absolute and relative concentrations of various species, the length of DNA fragments, and the conditions under which the reaction takes place (Hames).

In one hybridization method, a selected gene probe cDNA is labeled and added in single-strand form to a saturating mixture of mRNA transcripts. The presence of the probe-related transcript species can be assessed by the amount of labeled probe cDNA incorporated into double-strand material. This method is generally suitable for high- and moderate-abundance transcripts, but lacks the sensitivity required for the identification and analysis of low-abundance mRNAs due to high background levels.

Filter hybridization to a conventional cDNA library may be used to identify differences in low-abundance mRNAs from two different sources (Anderson). However, the one million or more library clones needed to insure the presence of virtually all low-abundance mRNAs effectively eliminates the utility of this technique for screening programs.

Nucleic acid subtraction techniques have also been proposed for use in studying differences in low-abundance mRNAs between related cell types (Maniatis). Here mRNA or cDNA preparations from two different sources are hybridized to completion, and the unhybridized remainder is examined for the presence of species of interest. This method, as it has been practiced heretofore, requires relatively large amounts of mRNA and/or cDNA starting material, especially where the species of interest is a relatively low-abundance mRNA. This limitation precludes the use of the method for many body-fluid or cellular samples of interest where the total concentration of unique species is low.

4. SUMMARY OF THE INVENTION

It is therefore one object of the invention to provide, for isolating RNA or genomic sequences which are unique to one of two mixtures, a method which overcomes many of the above-mentioned problems associated with the prior art.

A more specific object of the invention is to provide such a method which allows identification of unique species which are present at low concentration and/or low molar ratio in a mixture of genomic or RNA-derived duplex DNA fragments.

Another specific object of the invention is to provide such a method in which the degree of resolution and sensitivity can be increased as needed by repeated fragment amplification and/or selection steps.

Still another object of the invention is to provide a novel linker/primer DNA amplification procedure which is used in the method for unique-sequence isolation.

The invention includes, in one aspect, a method of isolating duplex DNA fragments which are unique to one of two fragment mixtures, i.e., fragments which are present in a mixture of duplex DNA fragments derived from a positive source, but absent from a fragment mixture derived from a negative source. In practicing the method, double-strand linkers are attached to each of the fragment mixtures, and the number of fragments in each mixture is amplified by successively repeating the steps of (i) denaturing the fragments to produce single fragment strands, (ii) hybridizing the single strands with a primer whose sequence is complementary to the linker region at one end of each strand, to form strand/primer complexes and (iii) converting the strand/primer complexes to double-strand fragments in the presence of polymerase and deoxynucleotides. After the desired fragment amplification is achieved, the two fragment mixtures are denatured, then hybridized under conditions in which the linker regions associated with the two mixtures do not hybridize. DNA species which are unique to the positive-source mixture, i.e., which are not hybridized with DNA fragment strands from the negative-source mixture, are then selectively isolated.

The fragment mixtures may be obtained from genomic DNA or derived from messenger RNA preparations. In one preferred embodiment, the fragments in the two mixtures are each blunt ended, then ligated with separate blunt-end primers. The linker attached to the positive-source fragment has an internal restriction site at which the fragment can be cut by a selected restriction endonuclease, allowing unique fragments which are isolated by the method to be cloned by insertion at a suitable vector cloning site.

Also in a preferred embodiment, the negative-source fragments are biotinylated, prior to hybridizing, and are present in large molar excess in the hybridization reaction. The negative-source fragments preferably contain an internal sticky-end restriction site at which the fragment can be cleaved, and biotinylated by filling with a polymerase in the presence of biotinylated nucleotides.

The species isolated in the above method may be further amplified and selected, to enhance enrichment of the unique sequence(s).

Also forming part of the invention is a method for amplifying duplex DNA fragments. The method includes attaching a double-strand linker to the fragments, and replicating the two strands in each fragment by denaturing the fragments to produce single fragment strands with linker-strand ends, hybridizing the single strands with a primer whose sequence is complementary to a linker-strand end on each fragment strand, to form strand/primer complexes, and converting the strand/primer complexes to double-strand fragments in the presence of polymerase and deoxynucleotides. The fragment-replication steps are repeated until a desired degree of amplification is achieved.

These and other objects and features of the invention will become more fully appreciated when the following detailed description of the invention is read in conjunction with the accompanying drawings.

DETAILED DESCRIPTION OF THE INVENTION

I. Amplifying DNA Fragments

A. Sources of DNA Fragments

Figure 1:
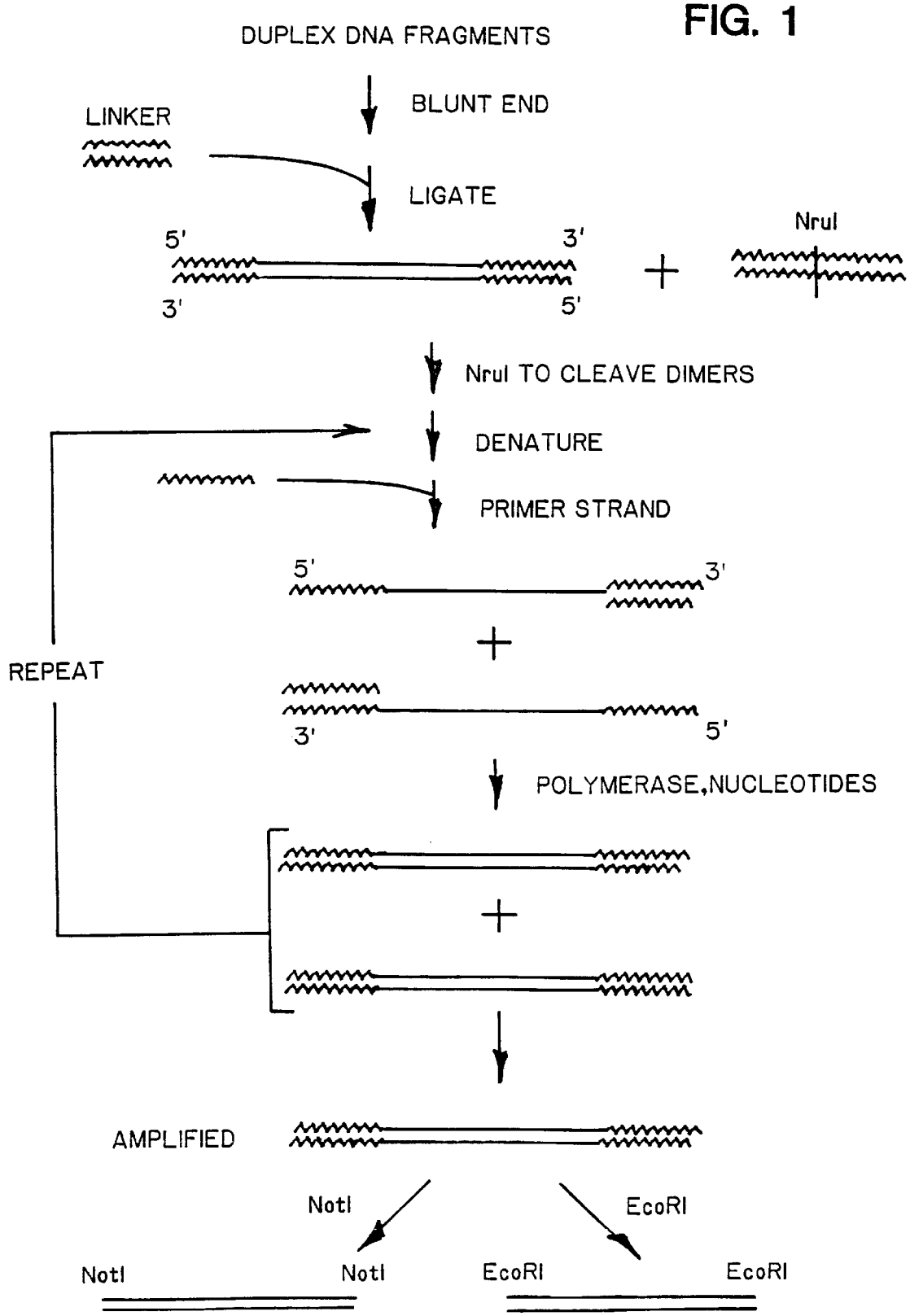
FIG. 1 is a flow diagram of the linker/primer duplex amplification method of the invention.

FIG. 1 illustrates the method of amplifying duplex DNA fragments according to the invention. The duplex fragments are typically present in a fragment mixture, and typically a mixture of cDNA fragments produced from messenger RNA (mRNA) transcript species, although genomic DNA fragments or linearized vectors or vector fragments are also suitable.

Methods for isolating mRNA species from cellular or body-fluid samples, such as serum or bile, are well known. One method involves formation of a vanadyl-RNA complex, extraction of protein with chloroform/phenol, and precipitation with cold ethanol. In a second method, the RNA is extracted from a guanidium isothiocyanate mixture with phenol, followed by a chloroform:isoamyl alcohol extraction, and precipitation of RNA from the aqueous phase with cold ethanol. The reader is referred to Maniatis, pp. 188–198, and references cited therein for details.

As a rule, eukaryotic mRNAs are characterized by a poly A termination sequence which allows isolation by affinity chromatography, using oligo dT bound to a solid support. In addition, or alternatively, total isolated RNA can be further fractionated by density gradient centrifugation, or agarose gel electrophoresis, to obtain a desired size fraction of RNA species.

Production of duplex cDNAs from the isolated mRNA transcripts is by conventional oligo dT or random priming of first strand synthesis. The former method is advantageous where duplex cDNAs derived only from poly A RNAs are desired. In this method, the RNA transcripts are primed with oligo dT, to promote first-strand cDNA synthesis by reverse transcriptase in the presence of all four deoxynucleotides. The 3' hairpin formed from the first-strand synthesis product is used to prime the synthesis of the second strand by *E. coli* DNA polymerase I, according to well-known methods (Maniatis, pp. 213–216).

The random priming method of cDNA duplex formation is preferred where (a) duplex formation is not to be limited to poly A species, or (b) full-length duplex cDNAs are not required. The method for first-strand cDNA synthesis utilizes an arbitrary sequence primer which is commercially available.

Following second-strand synthesis, the cDNA fragments are preferably blunt-ended, for example, by filling in sticky ends with the large fragment of *E. coli* DNA polymerase I (Klenow fragment) as described below in the Materials section.

Genomic DNA fragments, either in a fragment mixture or a purified preparation, are also suitable for amplification, according to the method of the invention. Genomic DNA from a selected cell source can be isolated by standard procedures, which typically include successive phenol and phenol/chloroform extractions with ethanol precipitation. The isolated DNA may be further fractionated to yield chromosomes or chromosomal regions of interest. The duplex DNA is fragmented preferably by partial or complete digestion with one or more selected restriction endonucleases, although mechanical shearing may be employed. The fragmented genomic pieces may be size fractionated, or further treated to remove repetitive DNA. Other sources of double-stranded DNA fragments can include extrachromosomal material, e.g., mitochondrial DNA, double-stranded DNA viruses, or viruses which have as part of their life cycle a double-stranded intermediate, e.g., a retrovirus.

Cellular sources of genomic DNA fragments or RNA transcripts used for producing cDNA fragments include cultured cell lines, or isolated cells or cell types obtained from tissue (or whole organs or entire organisms). Cell sources are of interest in a variety of subtraction techniques where it is desired to identify or isolate particular RNA transcripts or genomic material which are unique to one of two related cell sources. Body-fluid sources of DNA and/or mRNA transcripts are of interest primarily where the fluid is known or suspected to contain a viral agent or other microbe of interest. Example 3, for instance, describes cDNA fragment mixtures produced from RNA isolated from bile, taken before and after infection of cynomolgus monkeys with enterically transmitted non-A/non-B (ET-NANB) hepatitis virus.

Linearized or fragmented plasmid DNA, or fragmented phage DNA is another source of DNA fragments which one might wish to amplify. The vector DNA is obtained from purified plasmid or phage DNA according to conventional techniques, and linearized and/or fragmented by digestion with selected restriction endonuclease(s). Example 1 describes DNA fragments obtained by HaeIII digestion of phiX174 phage and linearized piAN13 plasmid.

B. Fragment Linkers

According to an important feature of the invention, the duplex DNA fragments to be amplified are ligated at their opposite end to a linker, to provide a priming sequence for strand duplication. The linker is preferably a short duplex DNA fragment, typically about 20–30 basepairs in length, having a defined basepair sequence. One end of the linker is designed for enzymatic ligation to opposite fragment ends. Where the fragments are blunt-ended cDNAs or genomic fragments, this linker end is also blunt, for ligation to the fragment ends in the presence of T4 DNA ligase, as described in Example 1. Where the DNA fragment mixture is formed by endonuclease digestion of genomic DNA, and produces fragments with sticky ends, the linkers can be prepared with complementary sticky ends at the fragment-ligation end.

Since the ligation reaction involving the linkers also produces linker-to-linker ligation, the linkers are preferably designed so that dimers can be selectively cleaved by restriction endonuclease digestion. This can be done by constructing the blunt end of the linker with a sequence representing one-half of a selected restriction-site sequence. The restriction site formed by blunt-end dimerization is preferably a rare cutter site, so that digestion of the fragments with the associated endonuclease, after linker addition to the DNA fragments, does not cleave a significant number of fragments internally, and thereby produce fragments with a linker at one end only.

Figure 2A:
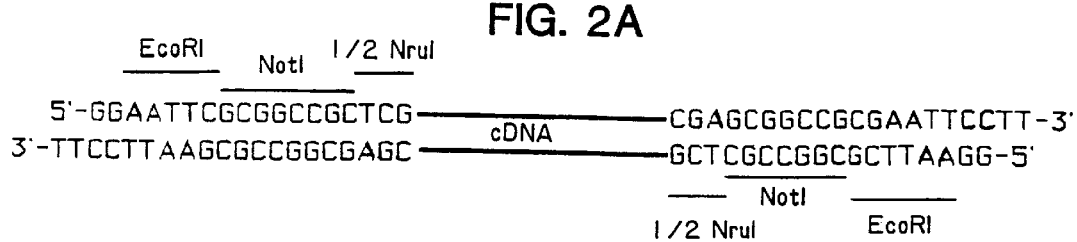
FIGS. 2A–2C shows the sequences of three exemplary linkers used in practicing the invention, after attachment to opposite ends of blunt-ended duplex fragments (solid lines)
Figure 2B:
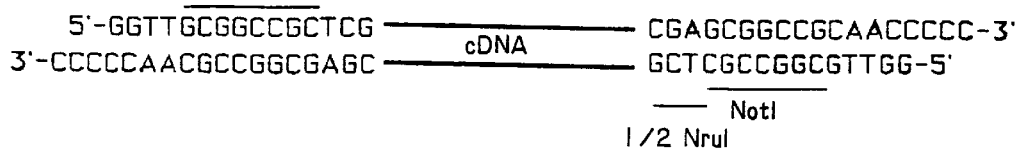
Figure 2C:
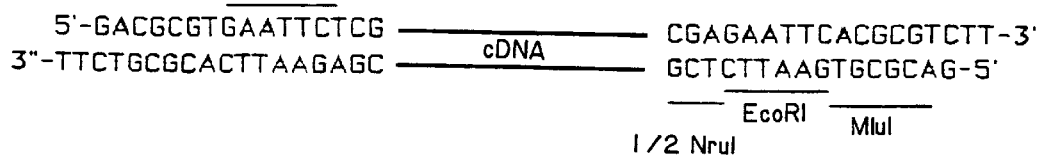
Figure 3:
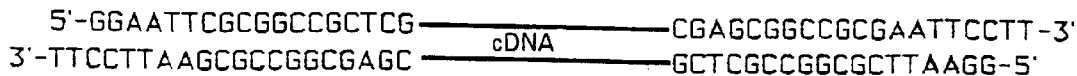
FIG. 3 illustrates one method for biotinylating amplified cDNA fragments, in practicing the invention.
Figure 3:
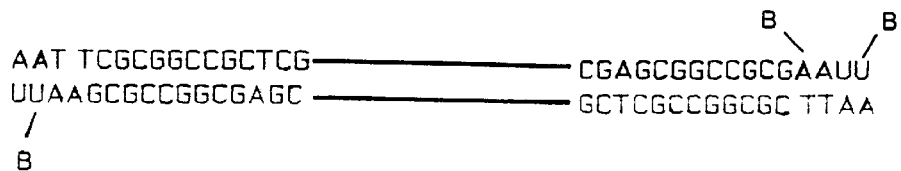

FIG. 2 shows DNA fragments (solid lines) with exemplary linkers A, B, or C attached to opposite fragment ends. As seen, each of the three linkers has one-half of an NruI site at its blunt end, whereby linker dimers formed by blunt end ligation can be cleaved by NruI digestion. It should be noted that linker ligation to the DNA fragments is directional, and linker self-ligation is limited to dimer formation, due to the one staggered end of the linker. The linkers are joined to blunt-ended fragments as indicated above, and as illustrated at the top in FIG. 1. It will be appreciated that analogous linkers with one sticky end for ligation to corresponding fragment sticky ends could be similarly employed.

Also as seen in FIG. 2, the linkers preferably include one or more internal restriction sites at which the fragments can be cleaved after amplification. The internal linker restriction site(s) can serve three purposes. First, where the amplified fragments are used in the DNA subtraction method described in Section II below, the restriction site can be used to cleave away a major portion of the linker in one of the two fragment mixtures, to prevent hybridization between linker regions in strands from the two different mixtures, where the same linker is used in the amplification of both fragment mixtures. Secondly, the linker cutting site(s) allows the amplified fragments (or the hybridized fragments in the Section II subtraction method), to be equipped with desired sticky end sites for cloning into a cloning vector. Thirdly, as will be seen in Section II, the linker restriction site may be used to create a single-strand end, for purposes of biotinylating the fragments. In particular, an internal EcoRI site produces an AATT overhang which can be filled in with commercially available biotinylated dUTP and dATP nucleotides.

Synthetic duplex oligonucleotide linkers having selected sequences, such as those shown for the three exemplary linkers in FIG. 2, can be prepared using commercially available automated oligonucleotide synthesizers. Alternatively, custom designed synthetic oligonucleotides may be purchased, for example, from Synthetic Genetics (San Diego, Calif.).

C. Fragment Amplification

The method steps described above are shown at the top in FIG. 1. These steps include obtaining duplex fragments, blunt-ending and attaching a linker to opposite fragments ends to produce linker-carrying fragments, such as illustrated in FIG. 2, and treating with a selected endonuclease to cut linker multimers at their blunt-end junctions.

The linker-fragments from above are amplified by the repeated fragment duplication according to the following steps. First, the fragments are mixed with a large molar excess of a single-strand oligonucleotide primer, typically a $10^6$–$10^9$ molar excess. The primer sequence is homologous to the fragment end linker; that is, the primer sequence and length is such as to promote hybridization to the complementary-linker regions of the two strands under moderately stringent reannealing conditions. Another requirement is that the primer, when hybridized to the linker region of the denatured fragment strands, be capable of priming polymerase-catalyzed strand replication; that is, the internal end of the primer provides a free 3'-OH. In the case of the linkers shown in FIG. 2, preferred primer sequences are:

d(5'-GGAATTCGCGGCCGCTCG-3') for linker A;
d(5'-GGTTGCGGCCGCTCG-3') for linker B; and
d(5'-GACGCGTGAATTCTCG-3") for linker C.

Single-strand oligonucleotide primers having the desired sequence are prepared by conventional methods or can be obtained from commercial laboratories, as above.

The denatured fragments and primer are cooled, typically between about 37–60° C., to allow primer hybridization with the fragment linker ends. The cooling period is kept quite short, typically less than about 5 minutes, to minimize strand-strand hybridization which would be expected on long-term reannealing. At this point, or at the primer-addition stage, the four deoxynucleotides and, optionally a DNA polymerase capable of catalyzing second-strand, primed replication are added, and the reaction mixture is brought to a temperature suitable for enzymatic strand replication.

In the method described in Example 1 below, the deoxynucleotides and DNA polymerase were added prior to fragment denaturation. After heat denaturing, the mixture was annealed at 50° C. for two minutes, then brought to 72° C. for 5–12 minutes for primed, second-strand replication. The DNA polymerase used is *Thermus aquatics* DNA polymerase (Taq DNA polymerase), which is relatively heat-stable at up to 95° C. for brief periods.

It will be appreciated from the above, and from FIG. 1, that the single added primer hybridizes with the 3'-end linker region in each DNA strand, and thus a doubling of fragment number occurs. The above replication procedure, which involves fragment denaturation by heating, cooling to form a fragment strand-primer complex, and second strand replication of the complex in the presence of DNA polymerase, is repeated until a desired concentration of fragments is achieved. In the above example, which employs a heat-stable Taq polymerase, the three replication steps are carried out simply by heating the fragment mixture to a denaturing temperature (above the $T_m$ of the fragments), cooling briefly to allow fragment/primer complex formation, and incubating for a period sufficient for second-strand synthesis.

Since the concentration of fragments doubles at each round of replication, a $10^3$ fold amplification can be achieved with about 10 rounds of replication, and a $10^6$ fold amplification with about 20 rounds of replication. Thus, starting picogram amounts of DNA fragments will yield microgram amounts of fragment material after about 20 rounds of replication.

Example 1 illustrates the application of the fragment amplification method to a linearized DNA plasmid (piAN13) and to a fragment mixture produced by HaeIII digestion of phage phiX174 fragments. Example 3 illustrates the application of the method to cDNA fragment mixtures derived from a mixture of mRNAs isolated from a bile sample.

D. Utility

The amplification method is useful for DNA duplex fragment amplification where limited amounts of genomic or cDNA fragment material is available and/or as a simple method of amplifying duplex DNA material where DNA sequences are unknown. For example, in the probe binding study reported in Example 3, the method was used to increase by several orders of magnitude, the number of cDNA fragments derived from bile infected with enterically-transmitted non-A/non-B hepatitis (ET-NANB) viral agent. The amplification allowed relatively small amount of viral agent present in the bile to be easily identified as an amplified cDNA fraction.

The method is useful for amplifying the amount of a fragment or fragments available for cloning, to enhance cloning efficiency. One advantageous feature of the method for cloning is the ability to provide the amplified fragments with end cloning sites suitable for the cloning vector which has been selected.

Another application, described in Section II below, involves amplifying two fragment mixtures, for use in DNA hybridization and subtraction, for isolating fragments which are unique to one of the two fragment mixtures.

The method can be applied to purified, enriched, or subfractionated DNA fragments, for increasing the amount of fragment material available for further processing, e.g., further enrichment. For example, in the fragment-isolation method described in Section II, the isolated unique sequence fragments can be further enriched by additional amplification and selection. As another example, a DNA subfraction obtained by gel electrophoresis can be selectively amplified. Here the fragment mixture, prior to fractionation, is equipped with an end linker, and the selected fragment band is further isolated, either in situ within the gel, or after selective elution, by addition of primer, polymerase, and nucleotides, with repeated heating and cooling replication steps.

II. Isolating Unique Sequences

A. Hybridizing Fragment Mixtures

Figure 4:
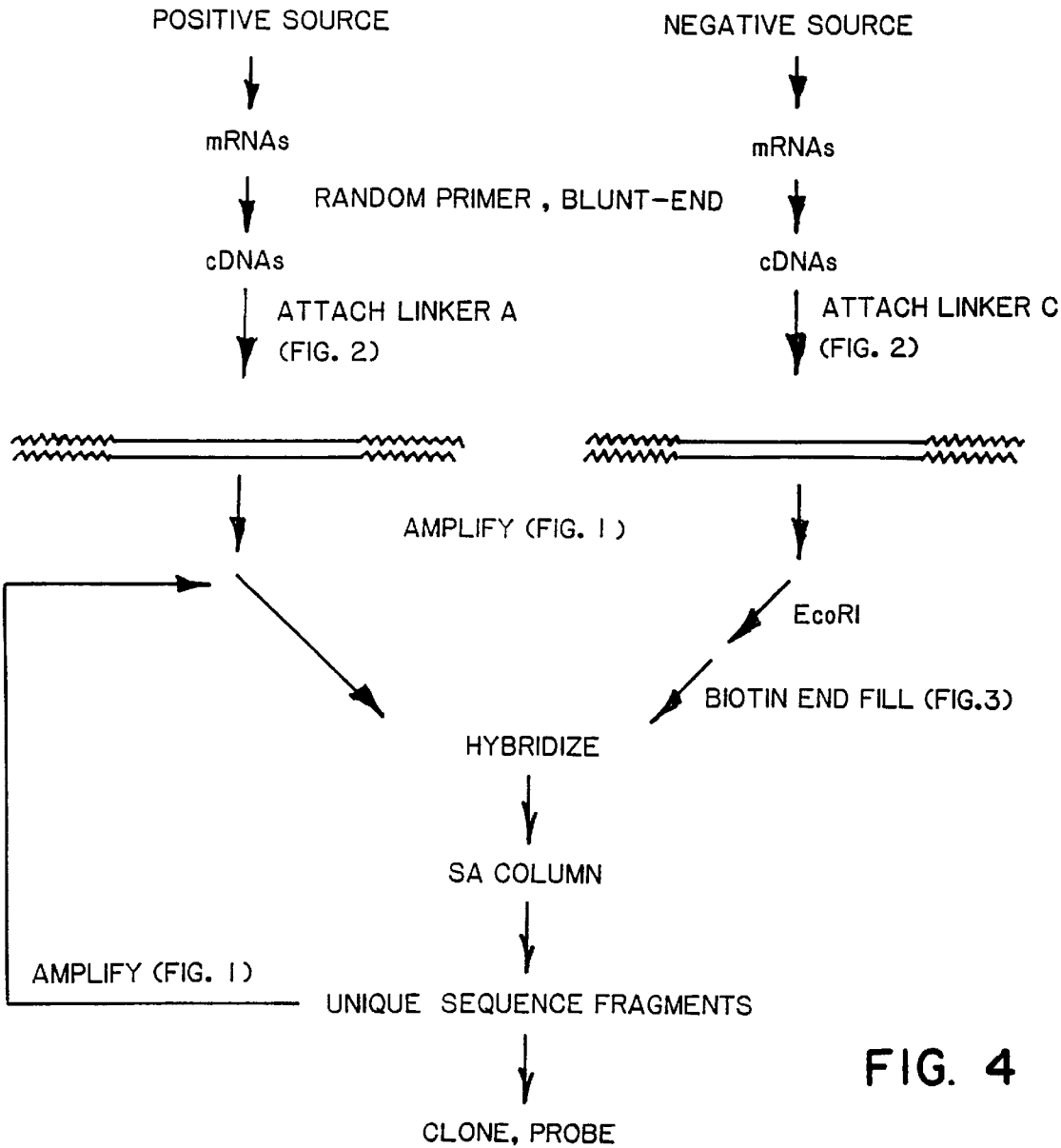
FIG. 4 is a flow diagram of the method of the invention for isolating DNA fragments which are unique to one fragment source.

FIG. 4 is a flow diagram of the method for isolating unique sequences from one of two fragment mixtures, according to the invention. The two fragment mixtures are referred to herein as positive- and negative-source mixtures, and are derived from positive and negative sources of nucleic acid species, respectively. The positive source may be any cell, cell group, tissue, organ, subcellular fractions, or other defined source of RNA transcripts or genomic fragments, including vector fragments, which contain a number of different-sequence species. The negative source is similar to the positive source, but lacks one or more positive source species.

By way of example, the positive and negative sources may be cell or tissue samples which are infected (positive source) and non-infected (negative source) with a microbial agent. Here the nucleic acid species associated with the infecting agent, either in the form of genomic material or RNA transcript species, are unique to the infected (positive) source. Similarly, the positive and negative sources may be a body fluid, such as serum or bile, from infected and non-infected subjects, respectively.

Where the present method is applied to the study of hereditary diseases, the positive source is typically a normal cell line or tissue capable of producing the full range of normal proteins associated with that cell, and the negative source is a genetically altered cell which is suspected of an altered or lost mRNA species. That is, the positive source will yield a normal mRNA species which is not present in the genetically altered, negative source.

As another example, it is known that malignant transformation in cells may be triggered by the activation of oncogenes, as evidenced by expression of new RNA transcripts associated with the malignant state. In applying the method of the invention to isolating and identifying such RNA species, the malignant cells or tissue serves as the positive source of unique (tumor-related) RNA species, and normal, non-transformed cells or tissue, as the negative source. Other examples of negative and positive sources of transcripts or DNA duplex fragments are contemplated.

The positive and negative sources shown in FIG. 4 yield mixtures of mRNA species, and these are converted to corresponding duplex DNA fragments as discussed in Section IA above. The duplex fragments in the two mixtures are blunt-ended and separately ligated at opposite fragment ends to a linker, as described in Section IB. The linker attached to the positive-source fragment is preferably different than that attached to the negative-source fragments. For example, in the method outlined in Example 1, the positive source fragments are ligated to linker A in FIG. 2, and the negative-source material, with linker C. Attaching linkers with different sequences to the two fragment mixtures avoids the problem of linker hybridization when the two mixtures are hybridized. Alternatively, the same linker may be attached to both fragment mixtures, if the linker contains a restriction site which allows substantially all of the linker to be removed by restriction endonuclease digestion from the negative-source fragment mixture before hybridization.

Each fragment mixture is then amplified by repeated replications, as described in Section IC above. In a preferred embodiment, the amplified, negative-source fragment strands are biotinylated or otherwise equipped with a ligand which can be used to selectively bind and remove strands or duplex species containing the ligand, by affinity chromatography. A variety of methods for biotinylating duplex fragments are available. For example, biotin-labeled deoxynucleotides, such as Bio-11-UTP and Bio-7-dATP, can be included in the amplification reaction mixture during the final rounds of replication. Duplex fragments are readily photobiotinylated by a standard procedure, as outlined in the protocol supplied by the manufacturer, Clontech (Palo Alto, Calif.). In one preferred method, the amplified fragments are treated with an endonuclease, such as EcoRI, which produces a 5'-AATT-3' sticky end. The sticky end is filled in with Klenow fragment in the presence of Bio-11-UTP and/or Bio-7-dATP, both of which are commercially available.

The two fragment mixtures are now combined and heat-denatured to single strand form. Preferably the negative-source fragments are present in substantial molar excess, typically about a tenfold excess, to insure that non-unique fragments in the positive-source mixture have a high probability of hybridizing with complementary strands from the negative-source fragments.

The positive- and negative-source fragments are hybridized under conditions in which hybridization between the linkers in the two different mixtures does not occur. This may be accomplished, as noted above, by using different-sequence linkers in the two mixtures, by cleaving the linkers from the negative-source fragment mixture prior to hybridization, or by hybridizing the fragment strands under conditions which preclude linker hybridization. Alternatively, the hybridization mixture may contain a large molar excess of primer oligonucleotides effective to hybridize with the positive-source linker end regions, thus preventing interstrand linker hybridization.

The hybridization reaction may be carried out according to classical hybridization techniques, such as detailed in Hames, or more preferably, by rapid hybridization techniques, such as the phenol emulsion reassociation technique (PERT), as described by Kohne, or the guanidinium thiocyanate method, as described by Thompson.

In the PERT hybridization method, the fragments are hybridized at a final DNA concentration of preferably between about 5–50 ug/ml in a phenol reaction mixture, and the reaction is carried out at 60–70° C. for up to 5–6 hours. The rate of annealing can be followed by hyperchromic shift at 280 nm or by diluting an aliquot of the reaction mixture with buffer, and quickly passing the material through a hydroxyapatite (HAP) column (Kohne).

In the guanidine thiocyanate method, the fragments are hybridized at a final DNA concentration of preferably between about 5–50 ug/ml in a 4M guanidine thiocyanate solution containing 8 mM DTT, and 20 mM Na citrate, pH 5.8. The mixture is heated to 65° C. for 5 minutes, to insure complete denaturation, then incubated at 26° C. for periods up to 72 hours, until complete hybridization has occurred (Thompson). The formation of DNA/DNA hybrids can be confirmed as above.

B. Isolating Unique-Sequence Fragments

Following hybridization, the reaction components are contacted with a solid support effective to preferentially bind non-unique fragments. In a preferred embodiment, where the negative-source strands are biotinylated, the reaction components are separated on an avidin or streptavidin column which is effective to bind all biotinylated strands and non-biotinylated (positive-source) strands which are hybridized therewith. Since the biotinylated strands are present in large molar excess, virtually all common-sequence strands from the positive-source will be bound to a complementary, biotinylated strand, and thus removed by the affinity chromatography.

Methods for separating the hybridization mixture on a streptavidin column are detailed in Example 2. Briefly, the hybridization mixture is passed through a column packed with streptavidin-agarose and washed extensively with elution buffer. The eluates from several washes are pooled and the nucleic acid is concentrated by ethanol precipitation, yielding a fragment mixture which is enriched for sequences which are unique to the positive-source material.

According to an important feature of the invention, the fragments isolated will contain the end linkers originally attached to the positive-source fragments, and thus can be further amplified, by the amplification method described in Section I. Where the positive-source linker is different than that on the negative-source fragments, additional amplification (employing the "positive-source" primer) will selectively amplify positive-source fragments, providing further enrichment of sequences which are unique to the positive source. As indicated in FIG. 4, the isolated amplified material may be rehybridized with the negative source fragments (which may be additionally amplified if necessary), and unique fragments again isolated by affinity chromatography, to enhance enrichment.

The final isolated fragments can be treated with DNA polymerase to ensure complete strand replication in the duplex species, then treated with a selected linker-site endonuclease, to provide fragment ends suitable for cloning or the like. Alternatively, or in addition, the isolated fragments can be radiolabeled according to known procedures, for use as a DNA probe.

C. Utility

Figure 5:
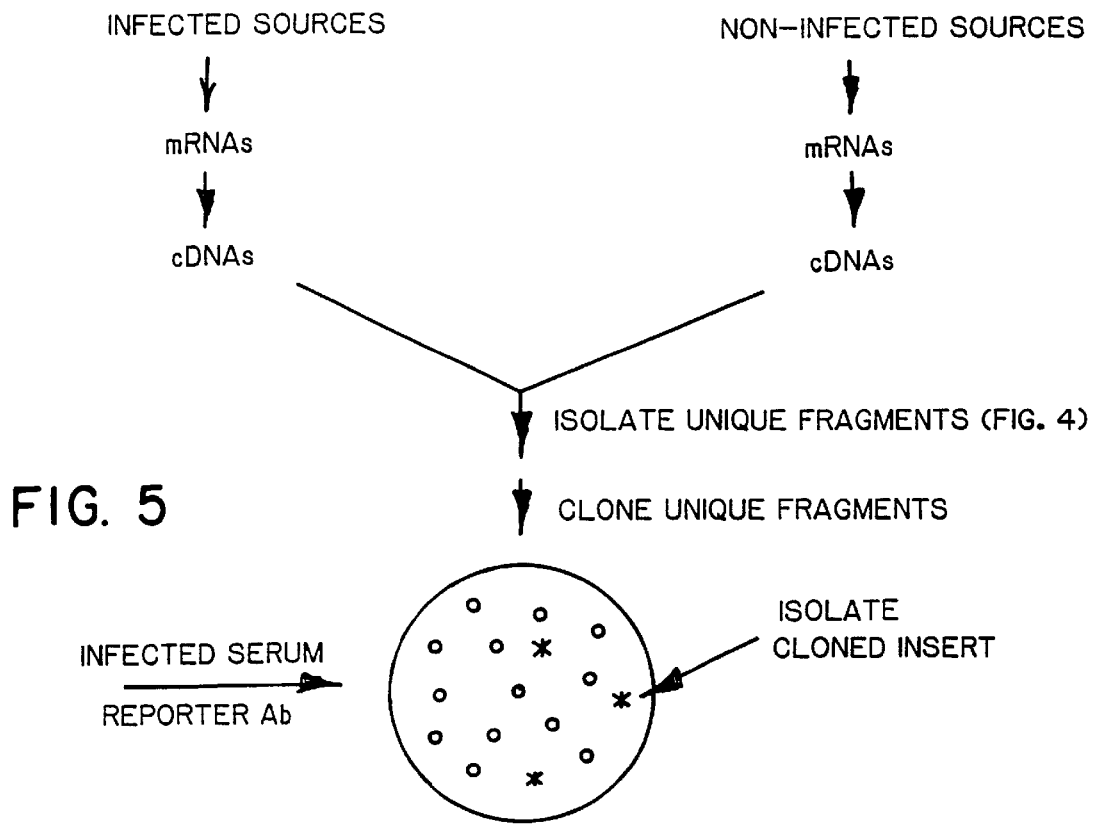
FIG. 5 illustrates the isolation method shown in FIG. 4 applied to isolation of an RNA-derived sequence which is unique to individuals infected with a given viral agent.

FIG. 5 illustrates one application of the subtraction method, for isolation and cloning of a viral agent present in RNA transcript in an infected source, such as selected tissue, or a body fluid, such as bile. Here RNA mixtures isolated from infected (positive) and non-infected (negative) sources are used to produce cDNA duplex fragment mixtures, which are blunt-ended, ligated to a selected linker, and amplified (Section I). After biotinylating the negative-source fragments, the two fragment mixtures are combined, denatured, reannealed, and separated by affinity chromatography (Section II). The isolated fragments, which contain a selected restriction site in their end-linker regions, are cut at this site and cloned in a suitable expression vector, such as the lambda gt11 vector. The resulting lambda gt11 phage constitute a fragment library enriched for sequences unique to the positive source material.

To select for desired isolates which produce a viral antigen, host cells are infected with library phage, and reacted with antiserum from an infected individual, to bind virus-related antibodies to host cells producing viral antigens. The cells are then washed to remove unbound antibody and contacted with a reporter-labeled anti-human IgG antibody, to label cells which have bound virus-specific antibodies. These cells are identified by the presence of the reporter. The vector(s) containing a viral insert can be used for continued antigen production, or as a source viral sequence probe.

Alternatively, the cloned isolated fragments in the fragment library can be identified and selected using DNA probes. By way of illustration, the fragment library generated as above can be replica plated and hybridized with labeled cDNA probes from infected and non-infected sources, prepared as in Section I. Probe hybridization can be carried out by conventional Southern blotting. Those library vectors which contain a viral-agent insert will hybridize with viral-agent cDNA probes present in the positive-source cDNA probes, but not with negative-source probes.

Methods similar to the DNA subtraction and probe selection method just described can be applied to identifying and isolating nucleic acid fragments which are unique to cells expressing oncogenes, or cells deficient in transcripts related to genetic disease.

Figure 6:
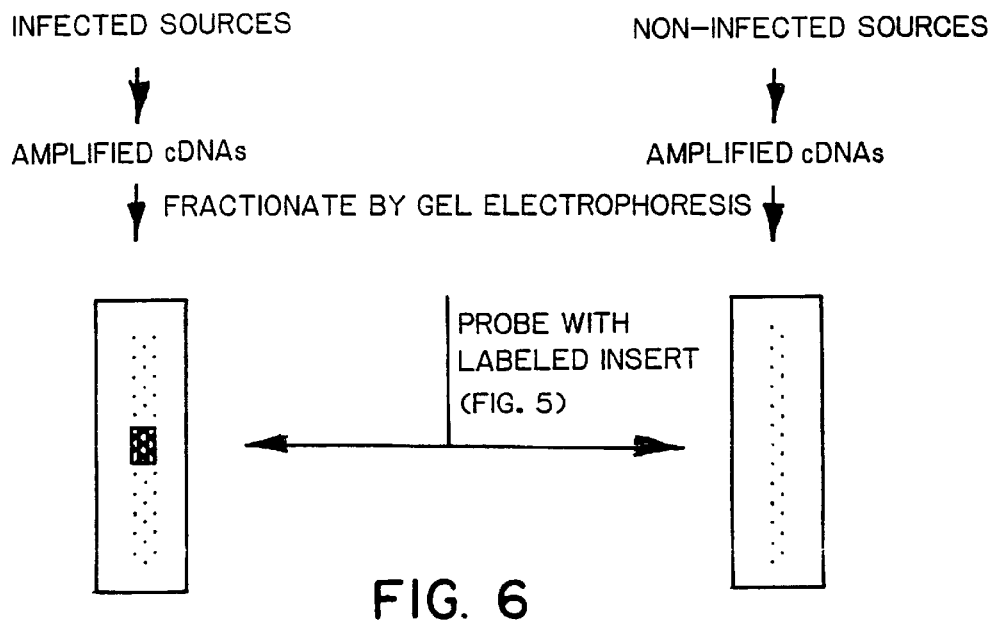
FIG. 6 illustrates the amplification method of FIG. 1, as it is used for confirming the presence of ET-NANB viral agent in bile from an infected animal, and for assaying the presence of the viral agent in infected individuals.

FIG. 6 illustrates how the amplification technique described in Section I can be used to confirm that the unique-sequence fragment clone(s) identified as above are in fact unique to the positive source. Here the two cDNA fragment mixtures prepared from positive and negative sources are amplified, as in Section I, and fractionated by gel electrophoresis. The size fractionated gel fragments are then transferred by conventional Southern blotting to filters and hybridized with the isolated cloned insert of interest, after probe labeling. If the probe sequence is unique to the positive source fragments, hybridization will be seen with amplified positive-source fragments only, as indicated in FIG. 6. As indicated in FIG. 6, the region of probe binding is fairly broad, as would be expected since the amplified fragments will have a range of sizes. This method of screening amplified cDNA fragments is detailed in Example 3, where the method has been used to confirm that an isolated ET-NANB fragment insert was unique to cDNA from an infected bile source.

The following examples illustrate the method of fragment amplification and fragment isolation described above, but are in no way intended to limit the scope of the method or its applications.

Materials

Plasmid piAN13 was obtained from Dr. Brian Seed (MIT). *E. coli* strain KM392, a suppressor positive strain, was obtained from Dr. Kevin Moore, DNAX, Palo Alto, Calif. *E. coli* strain LG75, a suppressor minus strain, was obtained from Dr. Brian Seed (MIT). Lambda phage Ch21 was obtained from Dr. Frederick Blattner (University of Wisconsin), and a NotI site was inserted between the EcoRI and HindIII sites (Ch21LJ), by replacing the 2 kb EcoRI/HindIII fragment with an oligonucleotide containing a NotI site. *E. coli* strain MC1061 harboring the P3 plasmid was obtained from Dr. Brian Seed (MIT).

Terminal transferase (calf thymus), alkaline phosphatase (calf intestine), polynucleotide kinase, *E. coli* DNA polymerase I (Klenow fragment), and S1 nuclease were obtained from Boehringer Mannheim Biochemicals (Indianapolis, Ind.); phiX174 fragments, produced by digesting the phiX174 phage to completion with HaeIII, were obtained from BRL Laboratories (Bethesda, Md.).

SmaI, EcoRI, NotI, T4 DNA ligase and T4 DNA polymerase were obtained from New England Biolabs (Beverly, Mass.); and streptavidin agarose, from Bethesda Research Labs (Bethesda, Md.). Low-gelling temperature agarose (Sea Plaque) was obtained from FMC (Rockland, Me.). Nitrocellulose filters were obtained from Schleicher and Schuell.

Synthetic oligonucleotide linkers and primers were prepared using commercially available automated oligonucleotide synthesizers. Alternatively, custom designed synthetic oligonucleotides may be purchased, for example, from Synthetic Genetics (San Diego, Calif.). cDNA synthesis kit and random priming labeling kits were obtained from Boehringer-Mannheim Biochemical (BMB, Indianapolis, Ind.).

Kinasing of single strands prior to annealing or for labeling is achieved using an excess, e.g., approximately 10 units of polynucleotide kinase to 1 nmole substrate in the presence of 50 mM Tris, pH 7.6, 10 mM $MgCl_2$, 5 mM dithiothreitol, 1–2 mM ATP, 1.7 pmoles gamma-$^{32}$p-ATP (2.9 mCi/mmole), 0.1 mM spermidine, 0.1 mM EDTA.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 ug of plasmid or DNA sequence is cleaved by one unit of enzyme in about 20 ul of buffer solution after 1 hr digestion at 37° C.; in the examples herein, typically, an excess of restriction enzyme is used to insure complete digestion of the DNA substrate.

Incubation times of about one hour to two hours at about 37° C. are workable, although variations can be easily tolerated. After each incubation, protein is removed by extraction with phenol/chloroform, and may be followed by ether extraction, and the nucleic acid recovered from aqueous fractions by precipitation with ethanol (70%). If desired, size separation of the cleaved fragments may be performed by polyacrylamide gel or agarose gel electrophoresis using standard techniques. A general description of size separations is found in *Methods in Enzymology* (1980) 65:499–560.

Restriction cleaved fragments may be blunt ended by treating with the large fragment of *E. coli* DNA polymerase I (Klenow reagent) in the presence of the four deoxynucleotide triphosphates (dNTPs) using incubation times of about 15 to 25 min at 20° to 25° C. in 50 mM Tris pH 7.6, 50 mM NaCl, 6 mM $MgCl_2$, 6 mM DTT and 0.1–1.0 mM dNTPs. The Klenow fragment fills in at 5' single-stranded overhangs in the presence of the four nucleotides. If desired, selective repair can be performed by supplying only one of the, or selected, dNTPs within the limitations dictated by the nature of the overhang. After treatment with Klenow reagent, the mixture is extracted with phenol/chloroform and ethanol precipitated. Treatment under appropriate conditions with S1 nuclease results in hydrolysis of any single-stranded portions of DNA. In particular, the nicking of 5' hairpins formed on synthesis of cDNA is achieved.

Ligations are performed in 15–50 ul volumes under the following standard conditions and temperatures: for example, 20 mM Tris-Cl pH 7.5, 10 mM $MgCl_2$, 10 mM DTT, 33 mg/ml BSA, 10 mM-50 mM NaCl, and either 40 mM ATP, 0.01–0.02 (Weiss) units T4 DNA ligase at 14° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 mg/ml total DNA concentrations (5–100 nM total end concentration). Intermolecular blunt end ligations are performed at 1 mM total ends concentration.

In vector constructions employing "vector fragments", the vector fragment is commonly treated with bacterial alkaline phosphatase (BAP) or calf intestinal alkaline phosphatase (CIP) in order to remove the 5' phosphate and prevent self-ligation of the vector. Digestions are conducted at pH 8 in approximately 10 mM Tris-HCl, 1 mM EDTA using about 1 unit per mg of BAP at 60° C. for one hour or 1 unit or CIP per mg of vector at 37° C. for about one hour. In order to recover the nucleic acid fragments, the preparation is extracted with phenol/chloroform and ethanol precipitated. Alternatively, religation can be prevented in vectors which have been double digested by additional restriction enzyme digestion and separation of the unwanted fragments.

EXAMPLE 1

Amplifying Duplex DNA Fragments

A. Modification and Amplification of piAN13 plasmid

Plasmid piAN13 carries a supF suppressor gene capable of suppressing an amber mutation. The plasmid was linearized by digestion with SmaI and ligated to the linker whose sequence is shown at A in FIG. 2, at a 1:100 molar ratio in the presence of 0.3–0.6 Weiss units of T4 DNA ligase. The linker sticky ends were filled in with Klenow fragment, conventionally, and the mixture was treated with NruI to cleave linker dimers. SmaI linkers were attached to the blunt-ends of the plasmid fragments under ligation conditions like those above. After treatment with SmaI to remove redundant SmaI linkers, the fragments were recircularized. This was done at a fragment concentration of about 1 ug/ml, in the presence of 4,000 units/ml DNA ligase, at about 14° C. for 18 hours. The resulting plasmids were thus modified to contain an A-sequence linker on either side of the original SmaI site.

E. coli strain MC1061 harboring the P3 plasmid was transformed with the recircularized plasmid, and selection for successful plasmids was made on the basis of bacterial growth in the presence of kanamycin, ampicillin, and tetracycline. Plasmids were isolated from the resistant bacterial colonies, and cut with SmaI to produce blunt-end, linearized fragments having the desired A-sequence end linkers.

To 100 ul of 10 mM Tris-Cl buffer, pH 8.3, containing 1.5 mM $MgCl_2$ (Buffer A) was added $1\times10^{-3}$ ug of the linearized plasmid, 2 uM of a primer having the sequence d(5'-GGAATTCGCGGCCGCTCG-3'), 200 uM each of dATP, dCTP, dGTP, and dTTP, and 5 units of Thermus aquaficus DNA polymerase (Taq polymerase). The reaction mixture was heated to 94° C. for 1 minute for denaturation, allowed to cool to 50° C. for 2 min for primer annealing, and then heated to 72° C. for 5–12 min to allow for primer extension by Taq polymerase. The replication reaction, involving successive heating, cooling, and polymerase reaction, was repeated an additional 25 times with the aid of a Perkin Elmer Cetus DNA thermal cycler.

B. Amplification of phiX174 Fragments

To a 50 ul solution containing 100 ng of the HaeIII blunt-end fragments was added 300 ng of the linker whose sequence is shown at C in FIG. 2, with ligation of the linker in the presence of DNA ligase being carried out as above. The mixture was treated with NruI to cleave linker dimers.

To 100 ul of Buffer A was added 1 ng of the phiX174/HaeIII fragments, 2 uM of a primer having the sequence d(5'-CACGCGTGAATTCTCG-3'), 200 uM each of dATP, dCTP, dGTP, and dTTP and 5 units of Taq DNA polymerase. The reaction mixture was heated to 94° C. for 1 minute for denaturation, allowed to cool to 50° C. for 2 min for primer annealing, and then heated to 72° C. for 5–12 min to allow for primer extension by Taq polymerase. The replication reaction steps were repeated 25 times, as above. The amplified fragments are referred to below as phiX/linker-C fragments.

A second preparation of phiX174 fragments was amplified by similar methods, but using the sequence-A linker employed in the piAN13 amplification. This preparation is referred to below as phiX/linker-A fragments.

EXAMPLE 2

Selection for piAN13 Sequences

A. Biotinylation of Amplified phiX174 Fragments

The amplified phiX174/linker-C fragment produced in Example 1B are treated with EcoRI to yield 5' protruding ends having an AATT sequence overhang. The fragments are biotinylated by Klenow fill-in reaction according to known procedures (Maniatis, pp. 113). Briefly, the reaction mixture consists of 100 ug/ml fragments in 100 mM potassium phosphate (pH 7.2), 2 mM $CoCl_2$, 0.2 mM DTT, 40 uM Bio-7-dATP, 100 uM dTTP, and 100 units/ml Klenow fragment. After incubation at 25° C. for 45 minutes, the reaction is terminated by heating at 65° C. for 10 minutes.

B. Hybridization Reaction

Amplified piAN13 vector is mixed at various mole ratios with the phiX/Linker-A fragments produced in Example 1B. Mixtures contained weight ratios of 1:100, 1:30 and 1:3 piAN13 to phiX/Linker-A fragments are prepared. Each mixture is then mixed with a 10-fold molar excess of biotinylated phiX/Linker-C fragments prepared as above, in an annealing buffer containing 2M guanidinium isothiocyanate (pH 5.8). The mixtures are heated to 65° C. for 5 minutes, then allowed to cool to 25° C. and hybridized for a 12-hour period.

C. Separation by Affinity Chromatography

A 1 ml silanized syringe plugged with silanized glass wool is packed with 0.5 ml streptavidin-agarose and washed with 10 mM Tris-Cl, 0.5 M NaCl, pH 7.0, containing 1 mM EDTA (elution buffer). A portion of each of the three hybridization mixtures from above is EtOH precipitated (70%), resuspended in 10 mM Tris HCl, 1 mM EDTA pH 7.0, and then loaded onto the column which is washed with several volumes of column elution buffer.

For each mixture, the eluate fractions from the streptavidin column are combined and the DNA concentrated by ethanol precipitation. The DNA is dissolved in Buffer A to a concentration of 0.01 ug/ml, and mixed with 2 uM of the above primer having the sequence d(5'-GGAATTCCGGCCGCTCG-3'), and 200 uM each of dATP, dCTP, dGTP, and dTTP, and 5 units Taq polymerase. The reaction mixture is denatured at 94° C. for 1 minute, cooled to 50° C. for primer annealing, and primer extension performed at 72° C. for 5–12 minutes.

The fragments from the each of the three eluate mixtures above are cut with NotI to produce NotI sticky ends in the linker regions of the fragments, as can be appreciated from FIG. 2A. The fragments (13 ug/ml) are mixed with 60 ug/ml NotI-digested phage Ch21aLJ, and inserted at the NotI site in the phage in the presence of T4 DNA ligase. After encapsidation, the phage are used to infect E. coli strain KM392, a suppressor-positive strain, and E. coli strain LG75, a suppressor-minus strain. The number of plaques produced in the KM392 strain provides a measure of total number of recombinant phage, since this strain is able to suppress the phage amber mutation, and thus allow phage expression of its A and B genes. In the LG75 strain, by contrast, only phage which have incorporated the piAN13 fragment produce plaques, since the sup F gene is required for growth of phage in suppressor minus bacterial strains. The ratio of plaques on the two host strains thus indicates the ratio of piAN13 fragments in the fragment mixtures. As a control, the ratio of fragments in the three mixtures before hybridization and streptavidin separation is also determined.

EXAMPLE 3

Screening Amplified cDNA Fragment Mixtures

A. Bile-Derived cDNAs

Two cynomolgus monkeys were intravenously injected with a 10% suspension of stool obtained from a human volunteer stool positive for ET-NANB, as evidenced by binding of virus-like particles (VLPs) in the stool to immune serum from a known ET-NANB patient. The animals developed elevated levels of alanine aminotransferase (ALT) between 24–36 days after inoculation, and excreted 27–30 nm VLPs in their stools in the pre-acute phase of infection. The animals became seropositive for VLPs in the inoculum.

The bile duct of each infected animal was cannulated and about 1 cc of bile was collected. RNA was extracted from the bile by hot phenol extraction, using a standard RNA isolation procedure. Double-strand cDNA was formed from the isolated RNA by a random primer for first-strand generation, using a cDNA synthesis kit obtained from Boehringer-Mannheim (Indianapolis, Ind.).

A cDNA fragment mixture from non-infected cynomolgus monkey bile was prepared similarly.

B. Stool-Derived cDNAs cDNA fragments obtained from human stool samples were prepared as follows. A 10% suspension of stool samples from healthy or ET-NANB-infected individuals was layered over a 30% sucrose density gradient cushion, and centrifuged at 25 kg for 6 hr in an SW27 rotor, at 15° C. The pelleted material contained 27–32 nm VLP particles characteristic of ET-NANB infection in the infected-stool sample. RNA was isolated from the sucrose-gradient pellets in both the infected and non-infected samples, and the isolated RNA was used to produce cDNA fragments as described in Example 1.

C. Amplification of the cDNA Fragment Mixtures

The cDNA fragment mixtures from infected and non-infected bile source, and from infected and non-infected human-stool source were each amplified by linker/primer replication, according to the method of the invention. Briefly, the fragments in each sample were blunt-ended with DNA Pol I then extracted with phenol/chloroform and precipitated with ethanol. The blunt-ended material was ligated with linker A shown in FIG. 2, under conditions like those described in Example 1, and the mixtures were digested with NruI to remove linker dimers. Each mixture was brought to a final concentration of 0.01 ug/ml in Buffer A, and to this was added 2 uM of a primer having the sequence d(5'-GGAATTCGCGGCCGCTCG-3'), and 200 uM each of dATP, dCTP, dGTP, and dTTP. The reaction mixture was heated to 94° C. for 1 minute for denaturation and allowed to cool to 50° C. for 2 min for primer annealing, and then heated to 72° C. for 5–12 min to allow for primer extension by Taq polymerase. The replication reaction, involving successive heating, cooling, and polymerase reaction, was repeated an additional 25 times with the aid of a Perkin Elmer Cetus DNA thermal cycler.

D. Screening Amplified cDNA Mixtures

The four amplified cDNA fragment mixtures from above were fractionated by agarose gel electrophoresis, using a 2% agarose matrix. After transfer of the DNA fragments from the agarose gels to nitrocellulose paper, the filters were hybridized to a random-labeled $^{32}$P 1.33 kb fragment associated with ET-NANB viral agent. The derivation and sequence of this fragment, which is carried in a pTZ-KF1 (ET1.1) plasmid identified by ATCC No. 67717, is described in co-owned patent application for "Enterically Transmitted Non-A/Non-B Hepatitis Viral Agent", filed on even date herewith. The cloned fragment was obtained by digesting the pTZ-KF1(ET1.1) plasmid with EcoRI, (ii) isolating the released 1.33 kb ET-NANB-fragment, and (iii) randomly labeling the isolated fragment.

The probe hybridization with the fractionated cDNA mixtures was performed by conventional Southern blotting methods (Maniatis, pp. 382–389). FIG. 6 shows the hybridization pattern obtained with cDNAs from infected (A) and non-infected (B) bile sources, and from infected (C) and non-infected (D) human stool sources. As seen, the ET-NANB probe hybridized with amplified fragments obtained from both of the infected sources, but was non-homologous to sequences obtained from either of the non-infected sources. This procedure demonstrates the utility of the described invention since hybridization analysis of an equivalent amount of cDNA prior to amplification would not have yielded detectable hybridization signal.

While the invention has been described with reference to particular embodiments, methods, construction and use, it will be apparent to those skilled in the art that various changes and modifications can be made without departing from the invention.

It is claimed:

1. A method of isolating duplex DNA fragments which are present in a mixture of different-sequence duplex DNA fragments derived from a positive source, but absent from a mixture of different-sequence duplex DNA fragments derived from a negative source, said method comprising attaching a double-strand linker to the positive-source fragments, and separately, to the negative-source fragments, by ligating the linker to both strands of said positive-source and negative-source fragments, at both ends of said positive-source and negative-source fragments, amplifying the number of each linker-carrying fragment in each fragment mixture by successively repeating the steps of (i) denaturing the fragments to produce single fragment strands with linker regions at each strand end, (ii) hybridizing the single strands with a single-strand primer whose sequence is complementary to the linker region at one end of each strand, to form a strand/primer complex, and (iii) converting the strand/primer complexes to double-strand fragments in the presence of polymerase and deoxynucleotides, denaturing the amplified fragments in the two amplified fragment mixtures and hybridizing the denatured fragments in the two mixtures under conditions in which the linker regions associated with the positive-source strands do not hybridize with the linker regions associated with the negative-source strands, and selectively isolating DNA species which are not hybridized with DNA fragment strands from the negative source.

2. The method of claim 1, wherein the fragment mixtures are derived from messenger RNA isolated from positive and negative sources, respectively, and the duplex fragments in each mixture are produced by converting the messenger RNA species in each mixture to double-strand cDNA fragments.

3. The method of claim 1, wherein the positive source is a body-fluid sample from an individual infected with a selected microorganism, and the negative-source is the same body fluid sample obtained from a noninfected individual.

4. The method of claim 1, wherein the fragments in each mixture have blunt ends, and the linkers attached to fragments have blunt ends which form, in a blunt end-to-blunt end linker dimer, a restriction site which can be cleaved with a selected restriction endonuclease.

5. The method of claim 4, wherein the linker attached to the positive-source fragments and the linker attached to the negative-sequence fragments have non-homologous sequences.

6. The method of claim 4, wherein the linker attached to the positive-source fragment has an internal restriction site at which the fragment can be cut by a selected restriction endonuclease, and the method further includes cloning isolated duplex DNA fragments, after digestion with said endonuclease, at a suitable vector cloning site.

7. The method of claim 1, wherein said hybridizing is carried out in a molar excess of the negative-source fragments.

8. The method of claim 1, wherein the negative-source fragments are biotinylated, prior to said hybridizing, and said removing includes removing biotinylated duplex fragments by affinity chromatography.

9. The method of claim 8, wherein the linkers attached to the negative-source fragments have an internal restriction site which can be cleaved with a selected restriction endonuclease to produce a sticky end, and the negative-source fragments are biotinylated by digesting the amplified fragments with the selected endonuclease, and filling in the sticky end with polymerase in the presence of biotinylated deoxynucleotides.

10. The method of claim 1, which further includes amplifying the number of each of the isolated DNA species by successively repeating the steps of (i) denaturing the fragments to produce single fragment strands, (ii) hybridizing the single strands with a single-strand primer whose sequence is complementary to the primer region at one end of each strand, to form a strand/primer complex, and (iii) converting the strand/primer complexes to double-strand fragments in the presence of polymerase and deoxynucleotides.

11. The method of claim 10, for further isolating duplex fragments which are unique to the positive-source mixture, which further includes denaturing the negative-source mixture and the amplified isolated DNA species, and hybridizing the denatured fragments in the two mixtures under conditions in which the linker regions associated with the positive-source strands do not hybridize with the linker regions associated with the negative-source strands, and selectively isolating DNA species which are not hybridized with DNA fragment strands from the second mixture.

12. A method of amplifying a mixture of different sequence duplex DNA fragments, comprising attaching a double-strand linker to the fragments, by ligating the linkers to both strands of the fragments, at both fragment ends, denaturing the fragments to produce single fragment strands with linker regions at both strand ends, hybridizing the single strands with a primer whose sequence is complementary to a linker region on each fragment strand, to form strand/primer complexes, converting the strand/primer complexes to double-strand fragments in the presence of polymerase and deoxynucleotides, and repeating said denaturing, hybridizing, and converting steps until a desired degree of amplification is achieved.

13. The method of claim 12, wherein the fragments are genomic fragments.

14. The method of claim 12, wherein the fragments are produced by converting messenger RNA species to double-strand cDNA fragments.

\* \* \* \* \*

(12) EX PARTE REEXAMINATION CERTIFICATE (7168th)
United States Patent
Reyes et al.

(10) Number: US 6,107,023 C1
(45) Certificate Issued: Nov. 17, 2009

(54) DNA AMPLIFICATION AND SUBTRACTION TECHNIQUES

(75) Inventors: Gregory R. Reyes, Palo Alto, CA (US); Jungsuh Kim, Palo Alto, CA (US)

(73) Assignee: Ladatech, LLC, Larchmont, NY (US)

Reexamination Request:
No. 90/008,996, Jan. 18, 2008

Reexamination Certificate for:
Patent No.: 6,107,023
Issued: Aug. 22, 2000
Appl. No.: 07/208,512
Filed: Jun. 17, 1988

(51) Int. Cl.
*C12Q 1/68* (2006.01)
*C12N 15/10* (2006.01)

(52) U.S. Cl. .......................... 435/6; 435/91.1; 435/91.2; 536/24.2; 536/24.3; 536/25.4; 536/24.33

(58) Field of Classification Search ............ None
See application file for complete search history.

(56) References Cited

U.S. PATENT DOCUMENTS 5,093,245 A    3/1992   Keith et al.

FOREIGN PATENT DOCUMENTS

EP    0 201 184 A2    12/1986
WO    WO 89/12695 A1    12/1989

OTHER PUBLICATIONS

Helfman et al., "Identification of clones that encode chicken tropomyosin by direct immunological screening of a cDNA expression library," Proc. National Academy of Science, U.S.A., vol. 80, pp. 31–35, Jan. 1983.

Kimmel et al., "Preparation of cDNA and the Generation of cDNA libraries: Overview," Methods in Enzymology, National Cancer Institute, National Institutes of Health, vol. 152, pp. 307–316, 1987.

International Preliminary Examination Report for International Application PCT/US89/02646 (WO89/12695).

*Primary Examiner*—Padmashri Ponnaluri

(57) ABSTRACT

A method of isolating genomic or RNA-derived duplex fragments which are unique to one of two fragment mixtures. The fragments in positive-source and negative-source mixtures are separately equipped with end linkers, and each mixture is amplified by successive primed-strand replications, using a single primer which is homologous to the associated linker. The second-source linker is biotinylated, and the fragments in this mixture are hybridized in molar excess with the fragments in the positive-source mixture. DNA species which are not hybridized with the biotinylated species, i.e., species that are unique to the positive-source mixture, are isolated after removal of hybridized species by affinity chromatography. Also disclosed is a method of amplifying a mixture of DNA fragments by repeated linker/primer replication.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 12–14 is confirmed.

New claim 15 is added and determined to be patentable.

Claims 1-11 were not reexamined.

*15. The method of claim 12 wherein the linkers ligated to the ends of the fragments are the same.*

\* \* \* \* \*